US00PP27433P2

(12) United States Plant Patent
Hansen et al.

(10) Patent No.: US PP27,433 P2
(45) Date of Patent: Nov. 29, 2016

(54) ***SCHIZACHYRIUM* PLANT NAMED 'SMOKE SIGNAL'**

(50) Latin Name: *Schizachyrium scoparium*
Varietal Denomination: Smoke Signal

(71) Applicants: Hans A. Hansen, Zeeland, MI (US); Kevin A. Hurd, Austin, TX (US)

(72) Inventors: Hans A. Hansen, Zeeland, MI (US); Kevin A. Hurd, Austin, TX (US)

(73) Assignee: Walters Gardens, Inc., Zeeland, MI (US)

( * ) Notice: Subject to any disclaimer, the term of this patent is extended or adjusted under 35 U.S.C. 154(b) by 104 days.

(21) Appl. No.: 14/544,455

(22) Filed: Jan. 8, 2015

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Susan McCormick Ewoldt

(57) ABSTRACT

A new and distinct plant cultivar of little bluestem plant, *Schizachyrium scoparium* 'Smoke Signal' has a columnar, upright habit that resists lodging or arching. The foliage develops scarlet-red tones in late summer and becomes deep red-purple by early fall. The flowers remain effective with reddish-brown coloration into winter.

1 Drawing Sheet

Botanical classification: *Schizachyrium scoparium.*
Varietal denomination: 'Smoke Signal'.

BACKGROUND OF THE PLANT

The present invention relates to a new and distinct cultivar of *Schizachyrium scoparium* plant and will be referred to hereafter by its cultivar name 'Smoke Signal' the "new cultivar" and "the new plant." 'Smoke Signal' represents a new cultivar of little bluestem, an ornamental grass grown for landscape use. The new plant was the object of an open pollinated cross in the trial fields of a wholesale perennial nursery in Zeeland, Mich., USA with the female parent the unreleased proprietary plant identified only by the breeder number K08-03-01 (not patented). The male parent is unknown and could have been any one of a number of seedlings and named cultivars in the breeding area as the pollen is normally windborne.

The two inventors initially selected the new cultivar in the summer of 2010 from a trial plot in Zeeland, Mich., and the single plant was given the breeder code of KH9-08-01. In the summer of 2012 the new plant passed the final phase of evaluation.

*Schizachyrium* 'Smoke Signal' has been successfully propagated by culm division at the same nursery in Zeeland, Mich. since the spring of 2011. The resultant asexually propagated plants have remained stable and true to type for all traits of the original plant in successive generations.

BRIEF SUMMARY OF THE INVENTION AND COMPARISON

The following traits have been repeatedly observed and represent the characteristics of the new cultivar which in combination distinguish *Schizachyrium* 'Smoke Signal' from all other little bluestem plants known to the inventors:

1. Columnar, orthotropic, upright habit through fall resisting lodging or arching.
2. Foliage develops scarlet-red tones in late summer.

3. Fall foliage becomes deep red-purple.
4. Rachis remains effective into winter with reddish-brown coloration.

*Schizachyrium* 'Smoke Signal' compares most closely with the little bluestem cultivars: 'Carousel' U.S. Plant Pat. No. 20,948 and 'Blaze' (not patented). Compared with the female parent, 'Smoke Signal' has darker red to more deeper red-purple foliage and a tighter more columnar habit. The new plant differs from 'Carousel' in being significantly taller and more columnar in overall habit and having foliage that is darker red to red-purple in late summer to fall. The overall height of 'Carousel' is about 75 cm while that of the new plant is about 110 cm. Compared with 'MinnblueA' U.S. Plant Pat. No. 17,310 the new plant is similar in form but slightly shorter in habit, and develops red-purple foliage coloration rather than the blue-green of 'MinnblueA'. 'Smoke Signal' is more upright and columnar than 'Blaze' which has a tendency to lodge and develop arching stems. Foliage coloration of 'Blaze' does not reach the same intensity of red-purple as 'Smoke Signal'.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, intensity, source and direction may cause the appearance of minor variation in color. The plant in the photographs is a three-year old plant grown in a full-sun trial garden in Zeeland, Mich., USA with supplemental water and minimal fertilizer when needed.

DETAILED BOTANICAL DESCRIPTION

Figure 1:
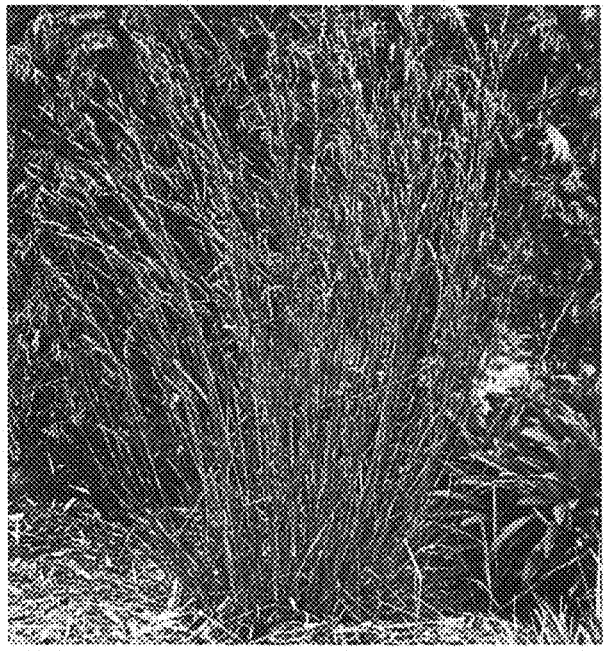
FIG. 1 shows the plant habit and foliage in flower.
Figure 2:
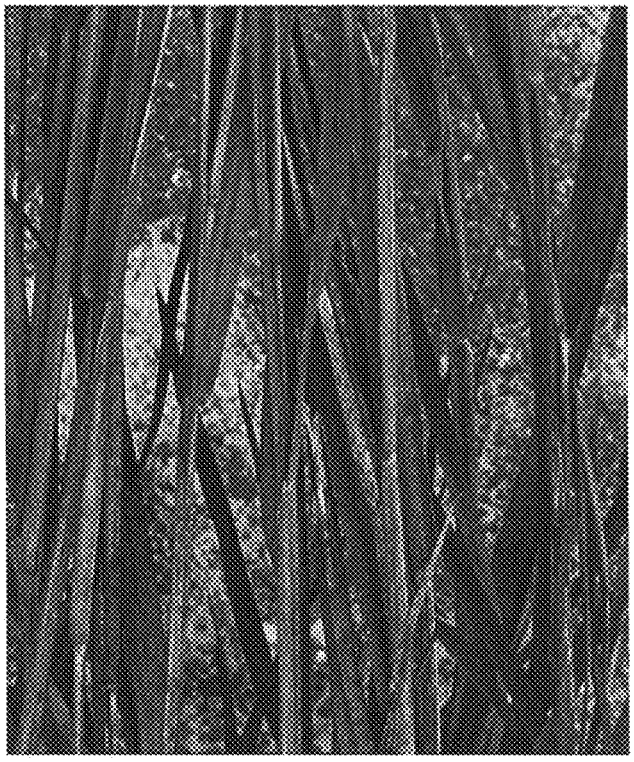
FIG. 2 shows a close-up of the foliage.

The following descriptions of *Schizachyrium scoparium* 'Smoke Signal' are of a three-year old full-sun trial plant grown in Zeeland, Mich. with supplemental water and minimal fertilizer as needed. The color references are in accordance with the 2001 edition of The Royal Horticultural Society Colour Chart except where common color terms of ordinary dictionary reference are used. The phenotype may vary slightly with different environmental conditions, such as temperature, light, fertility, moisture and maturity levels, but without any change in the genotype.

Female parentage: Unreleased proprietary plant identified only by the breeder number K08-03-01.

Male parentage: Open pollinated, parent unknown.

Propagation: By division of the culms or sterile plant tissue culture of micro-shoots.

Growth rate: Rapid, finishing in a 65 diameter mm container from a stage 3 tissue culture plant in three months; producing roots in tissue culture in three to four weeks.

Flowering effective period: Late summer through winter in Michigan with persistent seed heads.

Plant habit: Herbaceous perennial grass, compact and columnar of fine texture in the landscape with upright culms that resist lodging or arching.

Plant size: About 110.0 cm tall and about 45.0 cm wide.

Root description: Fibrous, wiry, deeply rooted up to about 90 cm long with fine branches.

Root color: Brown to off-white depending on soil type and age of roots with younger roots generally lighter in color.

Culm: Round in cross section; thin, wiry, strong; glaucous; glabrous; with foliage mainly on lower half; to about 110 cm long, average about 100 cm long and about 2.5 mm diameter near base; about 2.5 to 3.5 cm of culm exposed between leaves.

Culm color: Variable with season and light exposure, in late summer from nearest RHS 186 B to nearest RHS 59A to between RHS 187B and RHS 187C; from nearest RHS N199C with tinting of nearest RHS 182C to nearest RHS N186C in late fall and winter of area between leaves.

Nodes: Slightly swollen to about 4.0 mm at base; glabrous; internode length to about 15.0 cm, decreasing distally, average about 7.6 cm.

Node color: Nearest RHS N187A by mid-summer and into winter.

Foliage: Leaves flat, alternate, linear, entire, glabrous, glaucous; apex narrowly acute, base sheathing and usually open with a long narrow split extending to near the node; sheath portion up to about 10.0 cm long on lowest leaves and about 5.0 cm on highest leaves; largest leaves lower on stem up to about 30.0 cm long and about 7.0 mm wide; upper leaves about 8.0 cm long and about 3.0 mm wide; four to nine leaves per culm.

Leaf color: Summer between RHS 138A and RHS 138B; fall and winter nearest RHS N187A with tinting of brown nearest RHS 186B; adaxial sheath nearest RHS 165B from fall into winter.

Venation: Parallel.

Vein color: Same as surrounding tissue on both abaxial and adaxial.

Ligule: Membranous, fringed apex, about 1.0 mm in length and width equal to leaf.

Ligule color: Nearest 161D.

Flower description: Branched raceme at distal four to six nodes; flower period late fall in Western Michigan; remaining effective into winter.

Rachis: Glaucous, glabrous; up to about 16.0 cm long, and about 0.5 mm diameter; average about 13.5 cm long and about 0.5 mm diameter; frequently with two to three rachis per node.

Rachis color: Variable depending on season and light exposure, between nearest RHS 161D and more brown than RHS 183B and more purple than RHS 177B.

Spikelet: In pairs adpressed to rachis; one sessile and one pedicellate; pedicellate spikelet sterile and reduced; sessile spikelet fertile, about 16.0 mm long and about 8.0 mm across.

Glumes: Paired; lemma surrounding inner palea; adhering to caryopsis.

Lemma: About 8.0 mm long and about 1.0 mm wide; acute apex; color nearest RHS 200C.

Palea: About 7.0 mm long and about 0.8 mm wide; acute apex; color nearest RHS 200D.

Awn: Long and thin; about 16.0 mm long and less than 0.5 mm wide; color nearest RHS 200C.

Spikelet hairs: About 3.0 mm long and less than 0.1 mm diameter; collective color nearest RHS 155B.

Reproductive:

*Androecium*.—Usually three. Anthers: oblong; basifixed; about 3.0 mm long and about 0.5 mm across; color nearest RHS 187B. Filament: very fine, about 0.2 mm diameter and 2.5 mm long; color nearest RHS 155D. Pollen: abundant; color nearest RHS 187B.

*Gynoecium*.—One. Style: plumose; about 2.5 mm long and about 1.0 mm across; color nearest RHS 186D. Stigmas: numerous, non-secund, surrounding style; color between RHS 59C and RHS 187D.

Seed: Caryopsis, enclosed in glume; ovoid with broadly acute apex; less than 1.0 mm long and 0.7 mm across; color variable, between RHS 200C and RHS N199D.

Pest and disease resistance: Generally free of pests and diseases, susceptibility or resistance beyond that typical of little bluestem has not been observed.

Hardiness: Hard from U.S.D.A. zones 3 to 9; able to withstand adverse weather and still remain upright; like most little bluestem the new plant is able to withstand some drought once established.

I claim:

1. A new and distinct ornamental cultivar of little bluestem plant, *Schizachyrium scoparium* plant named 'Smoke Signal', as herein described and illustrated, for landscaping the garden en masse or individually.

* * * * *